US00PP27048P3

(12) United States Plant Patent
Cornelis

(10) Patent No.: US PP27,048 P3
(45) Date of Patent: Aug. 9, 2016

(54) ***SPATHIPHYLLUM* PLANT NAMED 'SP6531'**

(50) Latin Name: ***Spathiphyllum* hybrid**
Varietal Denomination: SP6531

(71) Applicant: Daniel Cornelis, Melsen-Merelbeke (BE)

(72) Inventor: Daniel Cornelis, Melsen-Merelbeke (BE)

( * ) Notice: Subject to any disclaimer, the term of this patent is extended or adjusted under 35 U.S.C. 154(b) by 97 days.

(21) Appl. No.: 14/121,539

(22) Filed: Sep. 16, 2014

(65) Prior Publication Data

US 2016/0081253 P1 Mar. 17, 2016

(51) Int. Cl.
*A01H 5/02* (2006.01)

(52) U.S. Cl.
USPC ..... Plt./364

(58) Field of Classification Search
USPC ..... Plt./364
See application file for complete search history.

*Primary Examiner* — Annette Para

(57) ABSTRACT

A new and distinct *Spathiphyllum* cultivar named 'SP6531' is disclosed, characterized by dark green foliage, clear white inflorescence and distinctive busy basal growth. The new variety produces a high quantity of spathes all at once, and flowers at 11 weeks from GA3 induction. The new variety is a *Spathiphyllum*, typically produced as an indoor ornamental plant.

1 Drawing Sheet

Latin name of the genus and species: *Spathiphyllum* hybrid.

Variety denomination: 'SP6531'.

BACKGROUND OF THE INVENTION

The new cultivar is a product of a planned breeding program. The objective of the breeding program was to develop new *Spathiphyllum* varieties suitable for commercial pot production. The new variety originated from a cross pollination of two unnamed, proprietary, parents. The inventor has no record of the exact parents involved in the cross. The crossing was made during April 2005.

The new variety was discovered by the inventor, Daniel Cornelis, a citizen of Belgium, in February 2006 in a group of seedlings resulting from the crossing. The new cultivar was found in a commercial green house belonging to the inventor in Melsem-Merelbeke, Belgium.

Asexual reproduction of the new cultivar 'SP6531' was first performed at a commercial laboratory in Belgium by tissue culture in April of 2007. Subsequent propagation by tissue culture has shown that the unique features of this cultivar are stable and reproduced true to type.

SUMMARY OF THE INVENTION

The cultivar 'SP6531' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SP6531.' These characteristics in combination distinguish 'SP6531' as a new and distinct *Spathiphyllum* cultivar:

1. Dark green foliage.
2. Clear white inflorescence.
3. Distinctive bushy base due to a high number of shoots arising from the base of the plant.

4. High quantity of spathes produced at once.
5. Time to flowering 11 weeks from GA3 induction.

PARENT COMPARISON

The inventor is unable to compare the new variety to the parent, as he has no record of the actual parents used for the cross.

COMMERCIAL COMPARISON

'SP6531' can be compared to the commercial variety *Spathiphyllum* 'Mara' U.S. Plant Pat. No. 16,422. Plants of 'Mara' are similar to plants of 'SP6531' in most horticultural characteristics, however, 'SP6531' has darker and smaller leaves than 'Mara.' Additionally 'SP6531' produces many more shoots and has a smaller inflorescence than 'Mara.'

'SP6531' can also be compared to compared to the commercial variety *Spathiphyllum* 'Alfa CD' U.S. Plant Pat. No. 10,823. Plants of 'Alfa CD' are similar to plants of 'SP6531' in most horticultural characteristics, however, 'SP6531' has much darker leaves than 'Alfa CD.' Additionally 'SP6531' produces many more basal shoots per plant than 'Alfa CD.'

BRIEF DESCRIPTION OF THE PHOTOGRAPH

The accompanying photograph in FIG. 1 illustrates in full color a typical plant of 'SP6531' grown in a greenhouse in Apopka, Fla. This plant is approximately 9 months old, shown in a 6 inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SP6531' plants grown in a climate controlled greenhouse in Apopka, Fla., USA. Temperatures ranged from 20° C. to 25° C. at night to 25° C. to 32° C. during the day. No artificial light, photoperiodic treatments were given to the plants. Plants were treated with Giberellic Acid at 200 ppm, to induce spathe production in approximately 11 weeks. Plants were grown in approximately 70% shade. Measurements and numerical values represent averages of typical plant types. Botanical classification: *Spathiphyllum* hybrid 'SP6531'.

PROPAGATION

Time to initiate roots: Approximately 7 to 10 days at approximately 23° to 25° C.

Time to produce a fully rooted plantlet: Approximately 12 weeks at approximately 23° to 25° C.

Root description: Thick, fleshy roots with fine, fibrous lateral roots. Color near Greyed-Yellow 161C.

PLANT

Growth habit: Moderate, upright.

Plant shape: Upright, leaves only slightly arching out.

Height: Approximately 27 cm to top of foliar plane. Approximately 36 cm to top of tallest spathe.

Plant spread: Approximately 45 cm in a 6 inch pot.

Pot size of plant described: 6 inch.

Growth rate: Moderate.

Branching characteristics: No true branching. Leaves emerge direct from base of plant.

Number of clumps of leaves: Average 8 to 10 per plant.

Number of leaves per clump: Average 12 to 16.

Age of plant described: Approximately 9 months.

FOLIAGE

Leaf:

*Arrangement*.—Single leaves emerging basally.

*Average length* (*excluding petiole*).—Approximately 20 cm.

*Average width*.—Average range 6.5 to 7.5 cm.

*Shape of blade*.—Elliptic.

*Aspect*.—Slightly undulating and recurved.

*Apex*.—Moderately cirrose.

*Base*.—Attenuate.

*Margin*.—Entire.

*Appearance*.—Glossy upper surface, matte lower surface.

*Texture of top surface*.—Smooth.

*Texture of bottom surface*.—Smooth, veins protruding.

*Color*.—Young foliage upper side: Near Green137A. Young foliage under side: Near Green 138B. Mature foliage upper side: Near Green137A, but darker. Mature foliage under side: Near Green 137D.

Venation:

*Type*.—Pinnate.

*Main venation coloration upper side*.—Near Green 143C.

*Main venation coloration under side*.—Near Yellow-Green 143C.

*Lateral venation coloration upper side*.—Near Green 137A.

*Lateral venation coloration under side*.—Near Yellow-Green N144C.

Petiole:

*Length*.—Approximate range between 12 and 16 cm.

*Width*.—At geniculum: Approximately 0.5 cm. Above clump: Approximately 0.8 cm.

*Color*.—Near RHS Green 143C.

*Strength*.—Very strong.

*Other*.—Petiole wing present.

Geniculum:

*Length*.—Approximately 3.0 cm.

*Width*.—Approximately 0.5 cm.

*Color*.—Near RHS Green 143C.

Petiole wing/petiole sheath:

*Length*.—Approximately 10.5 cm.

*Width*.—Approximately 0.7 cm.

*Color*.—Near RHS Green 143A.

INFLORESCENCE

*Arrangement*.—Spathes with spadices held above or within the foliage on erect peduncles arising from the petiole sheath.

*Flowering habit*.—Continuous.

*Quantity of spathes per plant*.—On average 8 fully open spathes in good condition.

*Natural flowering season*.—Autumn to Winter.

*Time to flowering*.—11 weeks after standard Gibberellic acid treatment of 200 ppm.

*Fragrance*.—None.

*Self-cleaning or persistent*.—Persistent.

*Flower longevity*.—Flowers stay in good condition approximately 5 weeks on the plant.

Spathe:

*Aspect*.—Cupped.

*Length*.—Average range 6.5 cm to 9.0 cm.

*Width*.—Approximately 3.5 cm.

*Shape*.—Elliptic.

*Margin*.—Entire.

*Apex*.—Cirrose.

*Base*.—Cuneate, non-symmetrical.

*Color*.—Front when opening: Near RHS White 155C. Back when opening: Near RHS White 155C. Front when mature: Near RHS White 155C. Back when mature: Near RHS White 155C, mid-vein becomes Green 143C. Fading to: Near RHS White 155C, mid-vein and large lateral veins streaked near Green 143B, both sides.

Spadix:

*Shape*.—Columnar, arising from the top of the peduncle.

*Tip*.—Obtuse.

*Base*.—Obtuse.

*Length*.—Approximately 4.2 cm.

*Width*.—Approximately 1.5 cm.

*Color*.—When opening: Near RHS White 155C. Mature: Near RHS White 155C. Aging: Near RHS Yellow-Green 145D.

*Quantity of flowers per spadix*.—Approximately 100.

*Spadix flower arrangement*.—Bisexual, rounded.

*Spadix flower diameter*.—Approximately 0.2 cm.

*Spadix flower depth*.—Approximately 0.2 cm.

Peduncle:

*Length*.—Approximately 8 to 14 cm, measured from base, which emerges from leaf axil.

*Width*.—Approximately 0.35 cm.

*Color*.—Near RHS Green 143C.

*Strength*.—Very strong.

REPRODUCTIVE ORGANS

All flower parts and reproductive organs are highly reduced, to the point of immeasurable.

*Quantity of pollen*.—Abundant.

*Pollen color*.—Near RHS White 155C.

OTHER CHARACTERISTICS

Disease resistance: Neither resistance nor susceptibility to typical diseases and pests of *Spathiphyllum* have been observed. Typical diseases include *Myrothecium, Pythium* and leaf *Phytophthora*. Aphids, fungus gnats, mealy bugs thrips and white flies are typical pests.

Drought tolerance and cold tolerance: The new cultivar is a typical *Spathiphyllum*, cold tolerant to approximately 5 to 7° C. and does not tolerate drought.

Fruit/seed production: Not observed.

What is claimed is:

1. A new and distinct cultivar of *Spathiphyllum* plant named 'SP6531' as herein illustrated and described.

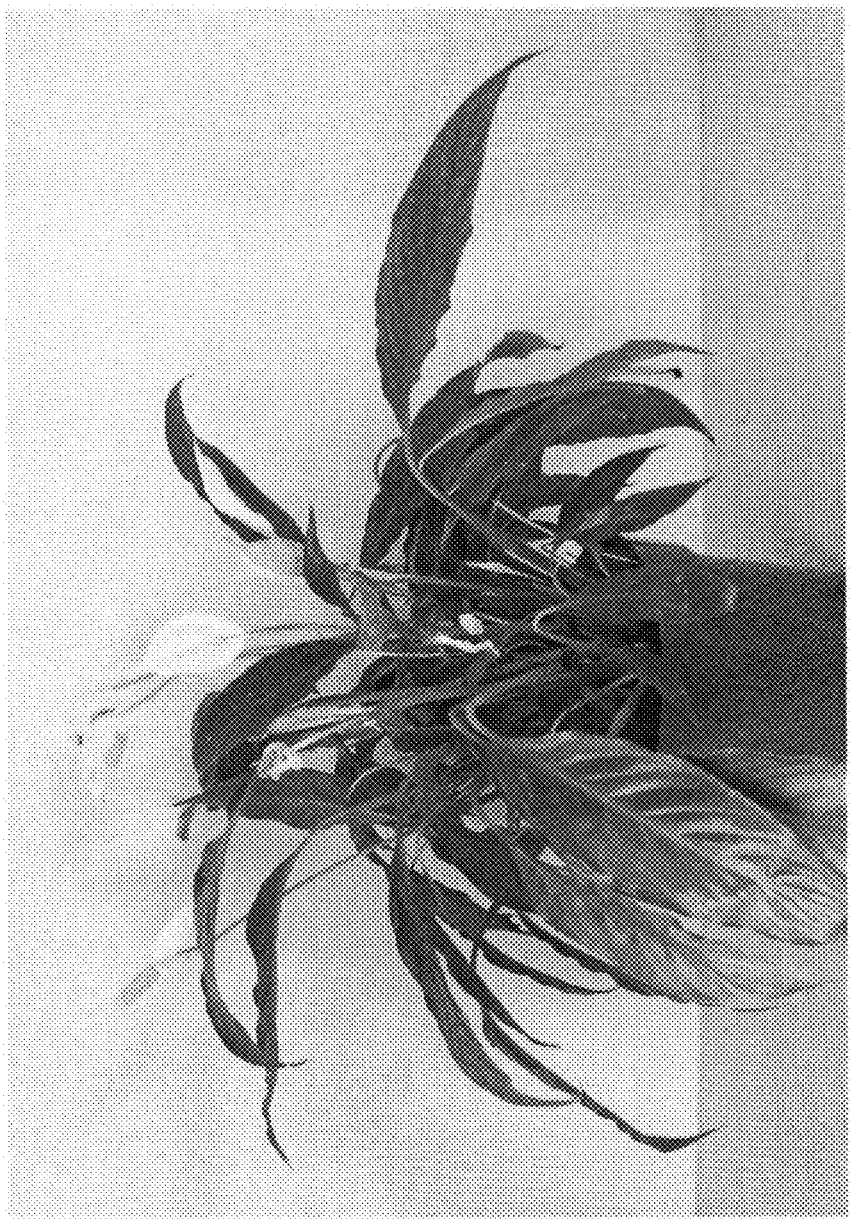

* * * * *